US006948365B2

United States Patent
Ambrosone

(10) Patent No.: US 6,948,365 B2
(45) Date of Patent: Sep. 27, 2005

(54) DYNAMOMETER AND RELATED ASSESSMENT METHOD

(75) Inventor: Mario Ambrosone, Avellino (IT)

(73) Assignee: K.S. Italia s.a.s. di Ambrosone Mario & Co., Avellino (IT)

( * ) Notice: Subject to any disclaimer, the term of this patent is extended or adjusted under 35 U.S.C. 154(b) by 0 days.

(21) Appl. No.: 10/488,709

(22) PCT Filed: Sep. 6, 2002

(86) PCT No.: PCT/IT02/00570

§ 371 (c)(1),
(2), (4) Date: Sep. 28, 2004

(87) PCT Pub. No.: WO03/022150

PCT Pub. Date: Mar. 20, 2003

(65) Prior Publication Data

US 2005/0061072 A1 Mar. 24, 2005

(30) Foreign Application Priority Data

Sep. 7, 2001 (IT) .................................. RM2001A0540

(51) Int. Cl.[7] .............................................. A61B 5/22
(52) U.S. Cl. ................................................. 73/379.01
(58) Field of Search ........................ 73/379.01, 379.03, 73/379.02; 473/463; 48/21; 600/587

(56) References Cited

U.S. PATENT DOCUMENTS

| 2,526,495 | A | * | 10/1950 | Meyer ...................... 73/379.02 |
| 4,674,330 | A | * | 6/1987 | Ellis ........................ 73/379.03 |
| 4,757,711 | A | * | 7/1988 | Omura ..................... 73/379.01 |
| 5,163,443 | A | * | 11/1992 | Fry-Welch et al. ......... 600/595 |
| 5,226,650 | A | * | 7/1993 | Suttner ...................... 473/463 |
| 5,398,696 | A | * | 3/1995 | Wiley ........................ 600/587 |
| 5,681,993 | A | * | 10/1997 | Heitman .................. 73/379.02 |
| 5,695,431 | A | * | 12/1997 | Bond et al. ..................... 482/1 |

* cited by examiner

Primary Examiner—Edward Lefkowitz
Assistant Examiner—Jewel V. Thompson
(74) Attorney, Agent, or Firm—Leffert Jay & Polglaze, P.A.

(57) ABSTRACT

Dynamometer (1) and related method for assessing the force (F) exerted at hand level, said dynamometer comprising a fixed frame (2), a pair of levers (3, 4) apt to be taken hold of by a user, at least one lever being movable, a contrast element having a known resistance parameter, connected to the movable lever in order to contrast the displacement thereof, and displacement measuring means (10), associated to the movable lever in order to measure the displacement ($\theta$) thereof.

20 Claims, 2 Drawing Sheets

DYNAMOMETER AND RELATED ASSESSMENT METHOD

BACKGROUND

The present invention refers to a dynamometer for assessing the force exerted at hand level and to a related assessment method.

As it is known to those skilled in the art, kinesiology is the discipline that, combining notions of anatomy, physiology and mechanics, studies human and animal motion, with specific regard to the muscular contraction mechanisms underlying said motion.

A specific branch of kinesiology studies hands. In that specific field, a type of clinical test often used for diagnostic purposes is the assessing of the muscular contraction force of hands and/or of individual fingers, and in particular the detecting of the force levels and the possible variations thereof in one or more sample muscles, optionally in response to various types of stimulus or stress.

Notwithstanding the remarkable importance of this type of tests in the highlighting of eventual functional problems in patients, to date no adequate technical means is available for the carrying out thereof.

In fact, said tests are mostly carried out manually by health workers, in particular by physician or physiotherapist operators, requiring remarkable care, skill and sensitivity thereby. However, even in the presence of these capabilities, the test results are anyhow related to the operator's subjective perception, and as such often they are repeatable neither by different operators, nor by the same operator. Moreover, a test thus carried out is scarcely sensitive to minimal force variations which might instead yield useful diagnostic indications.

In light of the above, this type of test is not accepted by the scientific and academic community.

Moreover, assessment methods of the force exertable by human body are known, which employ a weight of known entity connected to a displacement system of the rope-and-pulley type, said weight being lifted by the patient with a rope-applied handgrip. Other methods instead obtain the muscular force by measuring the flexion of semirigid levers caused by the patient's action.

However, the technical means employed in these latter methods merely provide approximate and low-sensitivity force measurements, moreover being rather awkward to use.

U.S. Pat. No. 2,526,495 describes a grip testing device comprising a couple of gripping bars apt to be pressed together by an operator and connected to light bulbs in such a manner that the latter are illuminated as a consequence of the pressing action exerted onto the gripping bars.

U.S. Pat. No. 5,398,696 describes a grip dynamometer useful in an isometric exercise method for lowering resting blood pressure, which dynamometer comprises a hand grip assembly associated with an arrow display.

SUMMARY

The technical problem underlying the present invention is to provide a dynamometer and a related assessment method of the muscular work overcoming the drawbacks abovementioned with reference to the known art.

This problem is solved by a dynamometer for assessing the force exerted at hand level.

According to the same inventive concept, the present invention further refers to a method for measuring the force exerted at hand level.

The present invention provides several relevant advantages. The main advantage lies in that it provides an instrument of appreciable sensitivity apt to assess the force exerted at hand level in a repeatable, simple and reliable manner.

DESCRIPTION OF THE DRAWINGS

Other advantages, features and modes of employ of the present invention will be made apparent from the following detailed description of some embodiments thereof, given by way of a non-limiting example. Reference will be made to the figures of the attached drawings, wherein.

DETAILED DESCRIPTION

Figure 1:
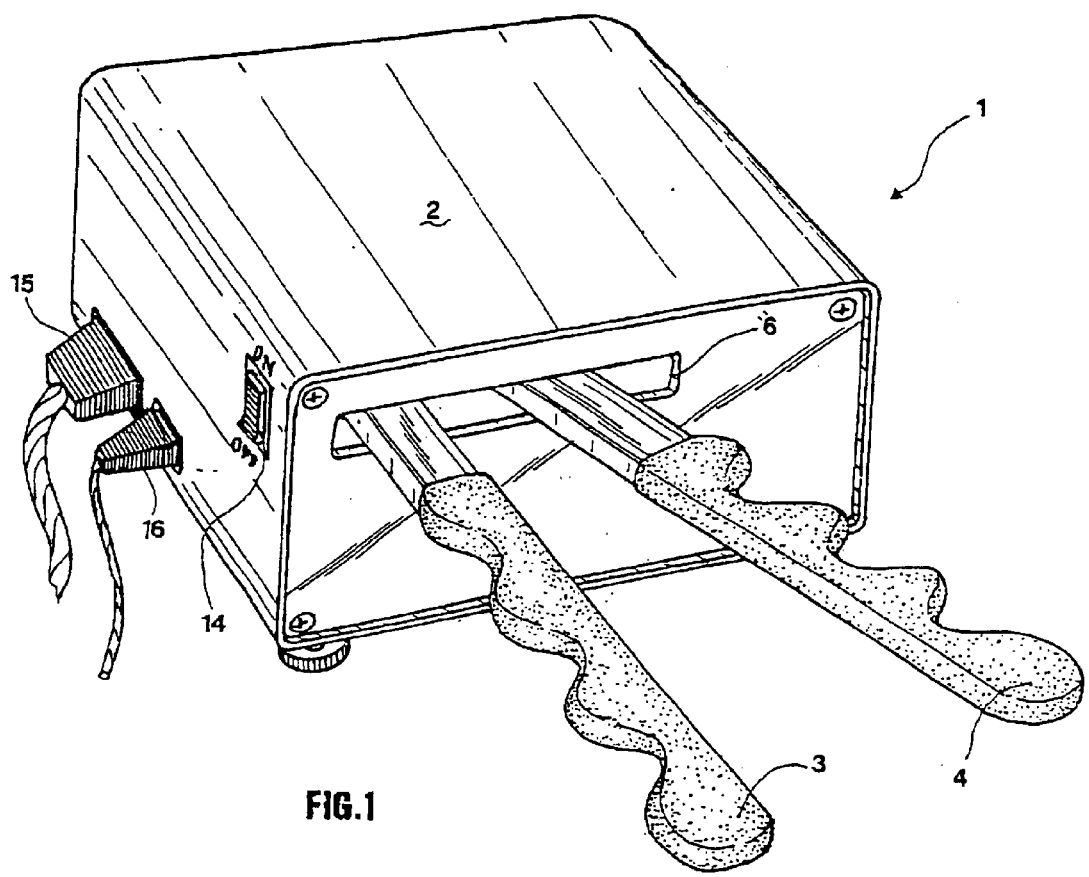
FIG. 1 is a perspective view of an embodiment of the dynamometer according to the present invention.

With initial reference to FIG. 1, a dynamometer for assessing the force exerted at hand level is generally indicated with 1. As it will be apparent from the following description, the dynamometer 1 is apt to assess the force exerted by a hand in its entirety as well as by its individual fingers.

The dynamometer 1 comprises a fixed frame, in form of a substantially parallelepiped-shaped outer casing 2.

Figure 2:
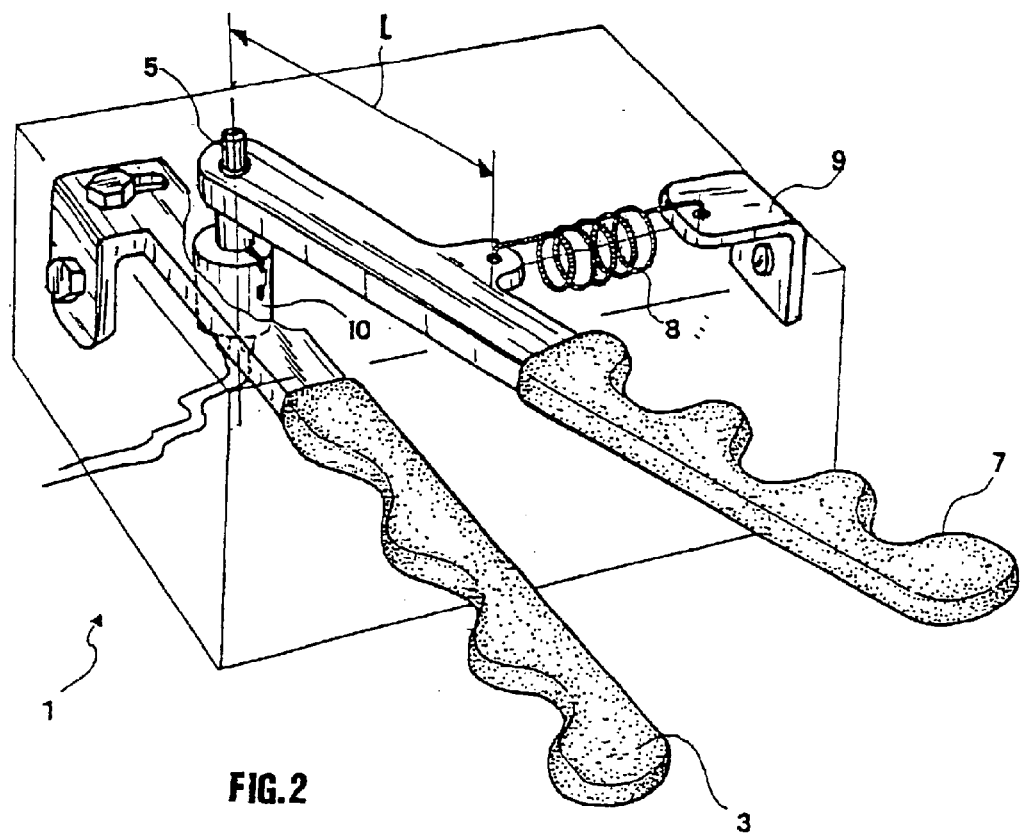
FIG. 2 is a partially sectional perspective view of the dynamometer of FIG. 1.

With reference now also to FIG. 2, to the frame 2 there are connected a first and a second lever, 3 and 4, respectively. In particular, the first lever 3 is made fixed to the frame 2 by conventional fastening means. The second lever 4 is instead movable with respect to the frame 2, and therefore with respect to the first lever 3, being rotatably connected to the frame by means of a shaft 5 fixed to the lever 4 itself.

Said connection of the levers 3 and 4 to the frame 2 is carried out at respective end portions of the levers themselves. Moreover, these levers project for a prevalent portion of their length outside of the frame 2, at a front slot 6 of elongated shape thereof.

Each lever 3, 4 bears, at said projecting portion, a handgrip profile, and in particular three bays 7, each apt to receive one finger.

Always with reference to FIG. 2, the movable lever 4 is further connected, at an intermediate portion thereof located internally to the frame 2, to a contrast element 8 apt to oppose a predetermined resistance to the motion of the lever 4. In particular, in the present embodiment this contrast element consists of a helical extension spring having known rigidity. This spring bears, at its ends, suitable hooking portions for connection to the movable lever 4 and to the frame 2, respectively. In particular, the connection of the spring 8 to the latter is carried out at an inner ledge 9 of the frame 2.

In a quiescent condition, i.e. in the absence of forces applied to the movable lever 4, the spring 8 lies in a condition of absence of tension, and it holds the former at a position angularly spaced from the fixed lever 3.

The dynamometer 1 further comprises an angular potentiometer 10 fastened to the frame 2, said shaft 5 being a part thereof. The potentiometer 10 is apt to measure the angular displacements of the movable lever 4 following a force exerted by the user against the elastic return force of the spring 8.

The potentiometer 10 is of a known marketed type, hence a further description thereof will be omitted.

In particular, a type marketed potentiometer suitable for implementing the dynamometer 1 is the "MEGGITT CITEC" one, having the following specifications: resistor element: CERMET; power rating; 2 W at 70°; maximum operating voltage: 315 W; resistance tolerance: +/−10%; thermal coefficient: +/−150 ppm/° C.; final resistance: 3 W max; rotation rating: 210° electrical, 270° electrical, 270° mechanical; rotational duration operations: 25.000; operating temperature range: −55° C. to +125° C.; body dimensions: diameter 21 mm, length 12.7 mm; shaft: diameter 6.35 mm, length 25 mm (metal); mounting bush: diameter 9.35 mm, length 10 mm (metal).

Figure 3:
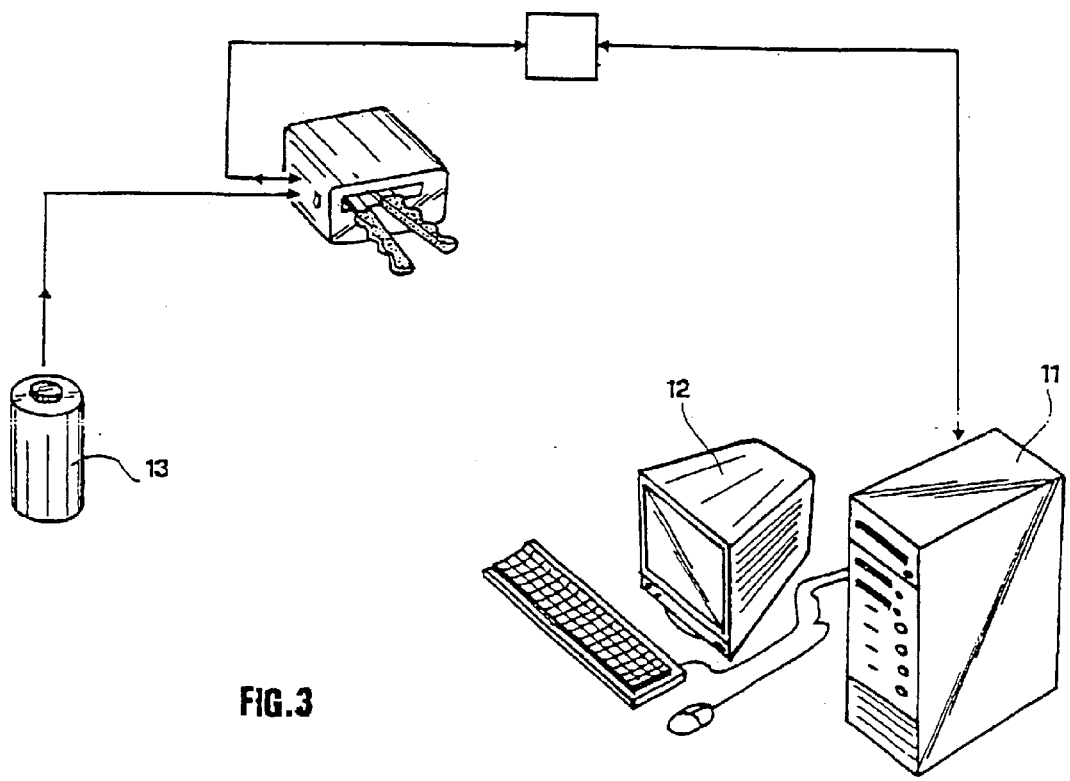
FIG. 3 is a block diagram of the dynamometer of FIG. 1.

As it is shown in FIG. 3, in the present embodiment the dynamometer of the invention also comprises hardware and software measurement processing means, in particular a PC processor 11 connected to the potentiometer 10 by conventional type data reception/transmission lines. In particular, the processor 11 is apt to compute the force exerted by the user according to the rigidity value of the helical spring 8 and to the displacement measurement provided by the potentiometer 10, as well as further derivative quantities, like e.g. the work performed by said force.

It will be understood that, from said data, the computing of the force exerted by the user against the elastic return force 8 can be carried out by means of mere trigonometric algorithms, adopting the known formulas for assessing the motive power applied to a lever, in this case the force exerted by the user, knowing the resisting force, in this case the elastic return force of the spring 8, and the related lever arms and considering that the fulcrum of the lever 4 is located at one end thereof, in correspondence of the axis of the shaft 5.

Figure 4:
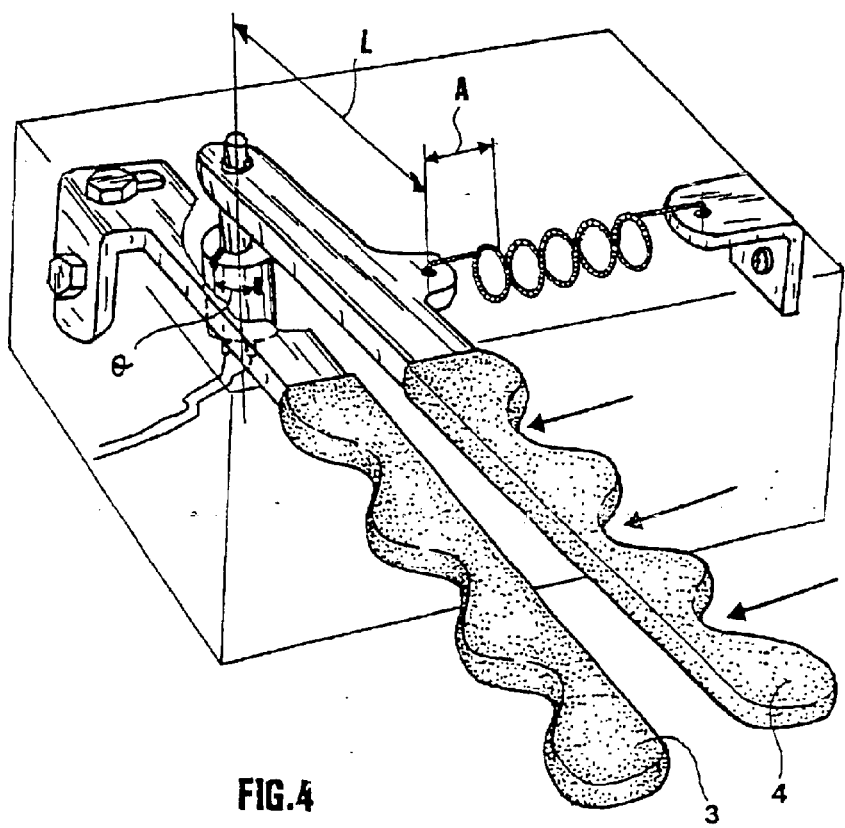
FIG. 4 is a partially sectional perspective view of the dynamometer of FIG. 1 during operation.

In particular, with reference to FIG. 4, indicating by L the (set) distance interposed between the hooking spot of the spring 8 to the movable lever 4 and the center of the pin 5, and by θ the angular displacement of the lever 4 itself caused by the action force exerted by the user thereon and measured by the potentiometer 10, the corresponding extension A of the spring 8 can be approximated as arc subtended by the angle θ, i.e.:

$$A \approx L\theta.$$

Alternatively, the extension A can be approximated as chord subtended always by the angle θ, i.e.:

$$A \approx 2L \sin(\theta/2).$$

Both such approximations are wholly acceptable within the context of the type of assessment to be carried out, also in light of the small angular displacements involved. Moreover, always by virtue of such small entity of the involved displacements, the transversal deformation of the spring 8 due to shear stresses is negligible.

Upon computing the extension A, the processing means 11 compute the return force F of the spring 8, according to the known relation:

$$F = k A,$$

where k indicates the (known) rigidity of the spring 8.

Then, the actual force exerted by the user can be estimated considering also the distance of the handgrip point from the fulcrum of the lever 4, a distance that varies according to the type of test carried out. Apparently, handgrip type being equal, also the resisting force F can be considered as an estimate of the motive power force actually exerted by the user.

Moreover, clinically an entity F' is often employed, having the dimensions of a work or energy, yet in turn indicated as force and assessed in (kg,m), and that, e.g. for the force F, can be computed as:

$$F' = F A.$$

Hence, also this quantity could be computed by the means 11.

Moreover, the processing means 11 are connected, always by conventional type data transmission lines, to means 12 for displaying the result of the measuring, that in the present embodiment is a monitor apt to graphically display the results.

The hereto-described processing and displaying means are well-known to those skilled in the art, being widely used to carry out biomechanical laboratory measuring for human motion analysis, hence a further description thereof will be omitted. In particular, these means provide a vast variety of processing and presenting options of the measurements, executable with known type hardware and software tools. Moreover, the former will typically have a user interface, comprising e.g. a keyboard, in order to enable the operator to input data related to the type of test carried out, and optionally to store the results thereof.

The dynamometer 1 further comprises a known type analog/digital converter interposed between the potentiometer 10 and the processing means 11, as well as conventional type power supply means 13, e.g. an accumulator connectible both to the potentiometer 10 and to the processor 11, optionally associated to a known type transformer. Such processing means enable also to carry out electronic calibration steps.

Of course, the dynamometer of the invention can also be power-supplied directly from the mains of the premises hosting it.

As it is shown in FIG. 1, at a sidewall of the frame 2 the dynamometer 1 further comprises an ON/OFF push-button 14, a connecting terminal 15 for connecting to the processor 11 and a terminal 16 for connecting to the accumulator 13. As also these elements and the associated components are of conventional type, a further description thereof will be omitted.

The operation of the dynamometer of the invention will hereinafter be made apparent. In particular, in order to carry out a kinesiological test for measuring the muscular contraction force at hand level, an operator, upon pre-arranging the dynamometer 1, will have the user grasp the two levers 3 and 4 of the dynamometer 1 with the fingers of the hand, left or right, to be involved in the measuring. e.g., a type of test provides the assessment of the force associated to the thumb and forefinger flexors. Therefore, in this test each one of these two fingers engages a bay 7 of a respective lever 3 or 4.

Then, the user exerts a force onto the two levers, and, acting against the return force of the spring 8, determines the longitudinal deformation thereof, and hence the angular displacement of the movable lever 4. This displacement is sensed and measured by the potentiometer 10, which transmits the related data to the processing unit 11, whereat the value of the force exerted is computed as above illustrated.

The quantities measured and those computed thereby are then graphically or numerically displayed onto the monitor 12, optionally also in terms of a time profile.

It will be appreciated that the dynamometer of the invention is quite flexible with respect to the option of assessing different entities associated to the force exerted by the user. In particular, those skilled in the art will appreciate that, besides the estimate of quantities such as the abovementioned force and work, from the force measuring carried out 'from the outside' like the abovedescribed ones there can be estimated, by known empirical relations, the 'inside' muscular contraction force.

Moreover, the dynamometer of the invention enables accurate and remarkably sensitive measuring. In particular, with the abovementioned components there can be measured quantities F' having a minimum value of about 2 $kg_f$ m and a maximum value of about 14 $kg_f$ m, with a resolution of about 200 $g_f$ m.

It will further be appreciated that the dynamometer of the invention has reduced dimensions and is extremely easy to employ, for the user as well as for the operator.

It will also be understood that the peculiar 3-bay structure of the lever handgrip enables the carrying out of a remarkably wide variety of tests, enabling different modes of handgrip.

It will be understood that the present invention is suitable for several embodiments alternative to the hereto-described one, some of which will briefly be illustrated hereinafter with reference to the sole aspects differentiating it from the hereto-considered first embodiment.

First of all, the dynamometer of the invention could have displacement measuring means alternative to the abovedescribed angular potentiometer. Of course, the type of these means depends also on the type of movability of the movable lever of the invention. The latter could, e.g., have a translational degree of freedom in alternative to or in association with the rotational one of the abovedisclosed embodiment. Moreover, the displacement measuring means could be directly connected to the elastic element rather than to the movable lever.

Furthermore, the dynamometer, and in particular the processing means thereof, could be preset to enable opposite-sense force measuring E.g., with reference to the abovedescribed embodiment, there could be provided a deformation both in extension and in compression of the elastic element.

The abovedescribed elastic element could further have a pre-tensioning state, i.e. a pre-loading state, also in the quiescent condition thereof. Moreover, a further embodiment provides the presence of a plurality of elastic elements arranged in series or in parallel, so as to increase the measuring range of the dynamometer.

Moreover, the dynamometer can comprise a contrast element different from the abovedescribed elastic element, like e.g. a hydraulic element. Therefore, the latter would have a known resistance parameter different from the rigidity of the elastic element itself.

Furthermore, the dynamometer levers could have a handgrip different from the abovedescribed one, apt to satisfy specific testing needs. In particular, in order to allow an optimum carrying out of the tests more frequently adopted in kinesiology, the movable lever could have a bay specifically shaped to receive a forefinger and optionally a further bay apt to receive a middle finger, and the fixed lever a bay specifically shaped to received a thumb.

According to a further simplified embodiment, the dynamometer of the invention can provide the measurement processing means to be directly incorporated into the frame receiving the levers introduced with reference to the abovedisclosed first embodiment. In this case, said means can also consist of a microprocessor, connected to the displacement measuring means by interposition of an analog/digital converter, it also directly received with the frame. Moreover, in this embodiment the means for displaying the result of the measuring could consist, instead of a monitor, of a simpler digital display apt to indicate to the operator the force level reached. Said digital display can be fixed with the frame or located thereabout. Moreover, in this case as well the dynamometer can enable an electronic calibration and allow resetting steps by operation of a suitable push-button.

In this latter embodiment the dynamometer of the invention is extremely easy to carry, thereby enabling to easily carry out 'on the field' force measuring i.e., not necessarily on clinical premises.

Moreover, the dynamometer of the invention can have selecting means, e.g. one or more push-buttons, located directly onto the casing or frame receiving the levers and apt to allow starting a measuring session and/or selecting the type of measuring to be carried out.

Furthermore, the levers of the dynamometer can also be both movable.

According to a further embodiment, the contrast element can have a selectivity variable resistance, and in particular an adjustable one, thereby enabling the measuring of different force ranges, i.e. the carrying out of a wider range of exercises. This adjusting of the resistance opposed to the motion of the movable lever is attainable, e.g., associating to the contrast element, for instance to the aboveintroduced helical spring, an actuator apt to modify the pre-loading level thereof. This actuator in turn can be controlled, with known modes and means, by the same user by operating suitable selecting means, e.g. a set of push-buttons each one corresponding to a respective resistance level. In the case of the helical spring, the actuator can consist of an electromagnetic motor and related transmission means. Moreover, the preset resistance level can also be displayed onto a suitable display.

By now, it will be apparent that the present invention provides also an assessment method for assessing the force exerted at hand level, comprising the steps of: having a user grasp, with one hand, a pair of levers as hereto-described with reference to the dynamometer of the invention; having the user exert a force against the resisting action of said contrast element; measuring the displacement given by the user to the movable lever; and computing the force exerted according to the already described modes.

The present invention was hereto described with reference to specific embodiments thereof. It is understood that there may be other embodiments afferent to the same inventive kernel, all falling within the protective scope of the appended claims.

What is claimed is:

1. A method for measuring a force (F) exerted at hand level, comprising the steps of:
   having a user grasp, with one hand, a pair of levers (3, 4) located on a frame (2), at least one (4) thereof being movable;
   having the user exert force (F) against a resisting action of a contrast element (8) connected to the at least one movable lever and having a known resistance parameter (k);
   measuring a displacement (θ) given by the user to the at least one movable lever; and
   processing the measuring carried out in such a way to compute the force (F) exerted according to the measured displacement and to the resistance parameter of the contrast element;
   wherein said step of measuring the displacement given by the user to the at least one movable lever (4) provides the measuring of an angular displacement (θ) of said lever.

2. The method according to claim 1, comprising the further step of computing the work (F') performed by the user upon exerting the force (F) to be measured.

3. The method according to claim 1, wherein said step of having a user grasp a pair of levers (3, 4) provides that the thumb and the forefinger of a user's hand each grasp a respective lever of the pair of levers, thereby enabling the assessment of the force of the flexors of such fingers.

4. The method according to claim 1, wherein said step of having a user grasp a pair of levers (3, 4) provides that the thumb grasp the fixed lever (3) and that the forefinger and the middle finger grasp the movable lever (4).

5. The method according to claim 1, wherein said resisting action is an elastic return force.

6. A dynamometer (1) for assessing the force (F) exerted at hand level, comprising:
- a fixed frame (2);
- a pair of levers (3, 4) apt to be grasped by a user, at least one (4) of which is movable with respect to said frame;
- a contrast element (8) having a known resistance parameter (k), connected to said at least one movable lever to contrast a displacement (θ) thereof;
- displacement measuring means (10), associated to said at least one movable lever to measure the displacement (θ) thereof following operation by the user; and
- means (11) for processing the measuring carried out;
- wherein the displacement measuring means (10) comprises means for measuring an angular displacement of the at least one movable lever at a rotatable connection between the at least one movable lever and the frame.

7. The dynamometer (1) according to claim 6, wherein at least one lever (3, 4) of said pair has an anatomical handgrip (7).

8. The dynamometer (1) according to claim 7, wherein said anatomical handgrip comprises three bays (7), each apt to receive a finger.

9. The dynamometer (1) according to claim 7, wherein a first lever (4) of said pair has a bay (7) specifically shaped to receive a forefinger and a second lever (3) of said pair has a bay (7) specifically shaped to receive a thumb.

10. The dynamometer (1) according to claim 9, wherein said first lever (4) is movable with respect to said frame (2) and said second lever (3) is fixed with said frame.

11. The dynamometer (1) according to claim 9, wherein said first lever (4) has a further bay (7) specifically shaped to receive a middle finger.

12. The dynamometer (1) according to claim 6, wherein said contrast element comprises an elastic element (8) having known rigidity.

13. The dynamometer (1) according to claim 12, wherein said elastic element comprises a helical extension spring (8).

14. The dynamometer (1) according to claim 6, wherein said contrast element (8) has an adjustable resistance.

15. The dynamometer (1) according to claim 14, wherein said contrast element comprises an elastic element (8) having known rigidity and said dynamometer comprises an actuator apt to modify the preloading level of said contrast element (8).

16. The dynamometer (1) according to claim 14, further comprising selection means operable by a user to select the resistance level of said contrast element (8).

17. The dynamometer (1) according to claim 14, further comprising display means apt to indicate the resistance level of said contrast element (8).

18. The dynamometer (1) according to claim 6, wherein said angular displacement measuring means comprises an angular potentiometer (10) located at said rotatable connection between the movable lever (4) and the frame (2).

19. The dynamometer (1) according to claim 6, wherein said processing means (11) of the measuring carried out is apt to output an entity (F') having the physical dimensions of work.

20. The dynamometer (1) according to claim 6, further comprising means (12) for graphically displaying the measuring carried out.

* * * * *